United States Patent [19]

Mizzoni

[11] 4,260,619
[45] Apr. 7, 1981

[54] 2-AMINOALKYL-5-PYRIDINOLS

[75] Inventor: Renat H. Mizzoni, Prescott, Ariz.

[73] Assignee: Ciba-Geigy Corporation, Ardsley, N.Y.

[21] Appl. No.: 122,463

[22] Filed: Feb. 19, 1980

Related U.S. Application Data

[63] Continuation-in-part of Ser. No. 35,668, May 3, 1979, abandoned.

[51] Int. Cl.³ .................. C07D 213/74; A61K 31/44
[52] U.S. Cl. ........................... 424/263; 546/300
[58] Field of Search ..................... 546/300; 424/263

[56] References Cited

U.S. PATENT DOCUMENTS 3,410,861  11/1968  McClosky ..................... 546/329
3,952,101  4/1976  Yu-Wen ....................... 546/300

OTHER PUBLICATIONS

Lezina et al., Chem. Abstracts, vol. 63, 13,049f–13,050–a, Nov. 8, 1965.
Smirnov et al., Chem. Abstracts, vol. 64, 5038–c–e Dec. 14, 1966.
Klingsberg, "Pyridine and Derivatives, " Part II, pp. 615–619, 643–646 & 772–777, Interscience Publ. (1962).

Primary Examiner—Alan L. Rotman
Attorney, Agent, or Firm—Theodore O. Groeger

[57] ABSTRACT

Secondary 2-aminoalkyl-5-pyridinols, e.g., those of the formula

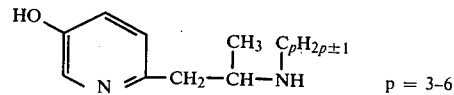

$p = 3-6$ and acid addition salts thereof are cardioprotective, e.g., antiischemic agents.

8 Claims, No Drawings

2-AMINOALKYL-5-PYRIDINOLS

CROSS-REFERENCE TO RELATED APPLICATION

This is a continuation-in-part of application Ser. No. 35,668, filed May 3, 1979 (now abandoned).

BACKGROUND OF THE INVENTION

Secondary 2-amino-1-hydroxyethyl-5-pyridinols, or "α-aminomethyl-5-hydroxy-2-pyridinemethanols...have direct bronchodilator action with minimal cardiac stimulation" according to Pat. No. 3,952,101, i.e., they have "greater activity on respiratory smooth muscle than on cardiac muscle."

Surprisingly, by the omission of said aliphatic 1-hydroxy- or methanolic function the contrary is achieved, i.e., cardioactive agents according to this invention are obtained, with negligible bronchodilator action.

SUMMARY OF THE INVENTION

The present invention concerns and has for its object the provision of new secondary 2-aminoalkyl-5-pyridinols, more particularly of those of Formula I

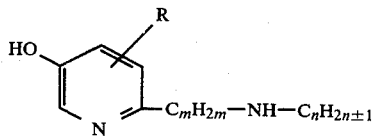

wherein R is hydrogen or methyl, m is an integer from 2 to 4 and n is an integer from 1 to 7; or of acid addition salts thereof; of corresponding pharmaceutical compositions and of methods for the preparation and application of these products, which are useful cardioprotective, especially antianginal agents.

DESCRIPTION OF THE PREFERRED EMBODIMENTS

In case R stands for methyl, this group may occupy any of the remaining 3-, 4- or 6-pyridinepositions. R represents, however, preferably hydrogen.

The alkylene group $C_mH_{2m}$ represents preferably 1,2-propylene, but also ethylene, 1,3-propylene, 1,2-, 1,3- or 1,4-butylene.

The lower aliphatic group $C_nH_{2n+1}$ is preferably lower alkyl, e.g., methyl, ethyl, n- or i-propyl, n-, i-or t-(butyl, pentyl, hexyl or heptyl); especially i-propyl.

Said group $C_nH_{2n-1}$ represents either lower alkenyl, e.g., allyl, methallyl, 2- or 3-(butenyl, pentenyl, hexenyl or heptenyl); or lower cycloalkyl, e.g., cyclopropyl, cyclobutyl, cyclopentyl, cyclohexyl or cycloheptyl; especially cyclopropyl or cyclohexyl.

The acid addition salts of the dibasic compounds of Formula I are preferably derived from the pharmaceutically acceptable acids listed below.

The compounds of the invention exhibit valuable pharmacological effects, for example, antihypertensive, but expecially cardioprotective, e.g., antiischemic (i.e., antianginal) properties. This can be demonstrated in animal tests, using preferably mammals, such as rats, cats and dogs, or isolated organs thereof. Said compounds can be administered to them enterally or parenterally, advantageously orally or intravenously, for example within gelatin capsules or in the form of starchy suspensions or aqueous solutions respectively.

The applied dosage may range between about 1 and 200 mg/kg/day, preferably between about 3 and 30 mg/kg/day i.v. or between about 10 and 100 mg/kg/day p.o.

Slight antihypertensive effects can be observed in spontaneous hypertensive rats or renal hypertensive dogs, either by sphygmomanometry at the rats' tail, or directly by means of a catheter placed into the dogs' femoral artery and a transducer; whereby the blood pressure is expressed in mm Hg.

The cardioprotective activity of said compounds is similar to that of nitroglycerin, propranolol and/or verapamil, which attenuate the electrocardiographic (ECG) manifestation (ST-T elevation) of myocardial ischemia produced by temporary coronary occlusion in anesthetized cats or conscious dogs. The latter were subjected to a left thoracotomy under pentobarbital anesthesia and artificial respiration. The pericardium was opened and a segment of the left coronary artery was exposed to allow the implantation of a silastic balloon occluder around it, which was exteriorized through the back of the neck at the shoulder blade and a protective jacket was fitted. The dogs were allowed to recover for 7 to 10 days and antibiotics are given the first four days after surgery. The dogs are then subjected to a priming occlusion during which no ECG-readings are taken. Thereupon 2 to 3 occlusions of 1-1.5 minutes duration are conducted in 5 minute intervals and the change in ST-T segment of the lead II·ECG is recorded and averaged before and at designated intervals after drug treatment, and the results are expressed as ratio of treated and untreated (control) response. Also permanent coronary occlusion is performed, venous blood samples are drawn for CPK-determinations 3, 6 and 24 hours after occlusion, whereupon the dogs are anesthetized, injected with Trypan blue dye, sacrificed with an overdose of sodium pentobarbital and the hearts dissected to estimate the necrotic tissue. According to the results obtained, the compounds of the invention significantly reduce the electrical, enzymatic and morphological changes (infarct size) caused by coronary occlusion in conscious dogs. Therefore, they are useful cardioprotective, especially antianginal agents. Moreover, said compounds are also valuable intermediates in the production of other useful products, especially of pharmacologically active compositions.

Particularly useful are compounds of Formula I, wherein R is hydrogen or methyl, m is the integer 2 or 3 and n is an integer from 2 to 6, or a pharmaceutically acceptable acid addition salt thereof.

Preferred compounds of this invention are those of Formula II

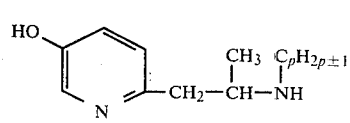

wherein p is an integer from 3 to 6, or a pharmaceutically acceptable acid addition salt thereof.

Outstanding are those compounds of Formula II, wherein $C_pH_{2p\pm1}$ represents i-propyl, t-butyl, allyl or cyclopropyl, or a pharmaceutically acceptable acid addition salt thereof.

The compounds of this invention are prepared according to conventional methods, for example by:

(a) hydrolyzing a compound of Formula III

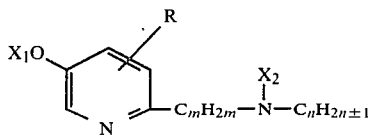

wherein $X_1$ and $X_2$ is an alkali metal or the monohalide of an alkaline earth metal, or at most one of $X_1$ and $X_2$ is hydrogen and the other is the acyl radical of an aliphatic or aromatic carboxylic or sulfonic acid, and the other symbols have the meaning given above; or (b) hydrogenating a Schiff's base of Formula IV

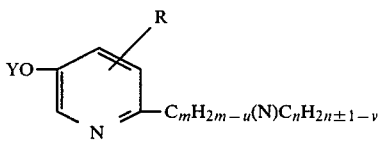

wherein one of u and v is the integer 1 and the other is 0, Y is hydrogen, or the acyl radical of an aliphatic or aromatic carboxylic or sulfonic acid, and the other symbols have the meaning given above, and hydrolyzing or alcoholyzing any resulting Y-ester; or (c) condensing a primary amine of Formula V

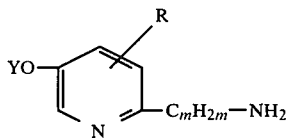

wherein the symbols have the above meaning, with a reactive ester of the alcohol $C_nH_{2n\pm1}$-OH in the presence of a strong base, and hydrolyzing or alcoholyzing any resulting Y-ester; or (d) reducing an amide of Formula VI

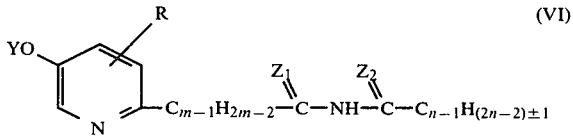

wherein one of $Z_1$ and $Z_2$ represents oxo and the other two hydrogen atoms, and the other symbols have the above meaning, with a simple or complex light metal hydride, and hydrolyzing or alcoholyzing any resulting Y-ester and, if desired, converting any resulting compound into another compound of the invention.

Said metallic substituent $X_1$ and $X_2$ in compounds III is preferably lithium, sodium or halomagnesium, whereas said acyl radicals are advantageously lower alkanoyl or alkanesulfonyl, unsubstituted or lower alkylated, alkoxylated and/or halogenated benzoyl, benzenesulfonyl or carbobenzyloxy, such as acetyl, propionyl, methanesulfonyl, benzoyl, p-toluyl, p-anisoyl, m-chlorobenzoyl, benzenesulfonyl, tosyl or carbobenzyloxy (benzyloxyformyl).

The hydrolysis of said compounds III is advantageously performed with water or, depending on the metallic or nonmetallic character of $X_1$ and $X_2$, with diluted inorganic or organic acids or based respectively, e.g., aqueous alkalies or acids, e.g., those listed below, preferably at or below room temperature, such as at about 0°, in case $X_1$ and $X_2$ is metallic, or above room temperature, such as 40°–120°, in case they are nonmetallic. Said carbobenzyloxy compounds III may also be cleaved hydrogenolytically, as known per se in the peptide-synthesis, i.e., with hydrogen in the presence of noble metal catalysts, e.g., palladium or platinum.

The metallic starting material III can be prepared by condensing compounds of the formulae

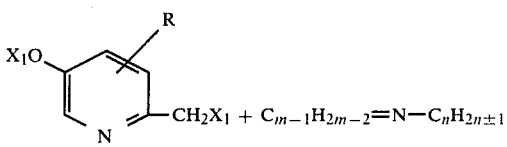

wherein $X_1$ is said alkali metal or alkaline earth metal halide, and all other symbols have the meaning given above, under anhydrous conditions, advantageously in polar diluents, such as open or cyclic ethers, e.g., diethyl ether or tetrahydrofuran, and at temperatures below room temperature, e.g., between about 10° and −20°. Alternatively, said acyl derivatives III are prepared by condensing compounds of the formula

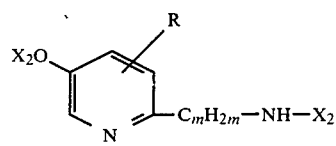

wheren $X_2$ is said acyl radical of an aliphatic or aromatic carboxylic or sulfonic acid, with a reactive ester of the alcohol $C_nH_{2n\pm1}$OH, mentioned below.

The Schniff's bases IV are conventionally hydrogenated, either with catalytically activated or nascent hydrogen, such as hydrogen in the presence of palladium, platinum or nickel catalysts, or generated electrolytically; or with simple or complex light metal hydrides, e.g., boranes, alane, or alkali metal boro- or cyanoborohydrides, such as sodium borohydride or cyanoborohydride. Any resulting Y-ester may be hydrolyzed or alcoholyzed in known manner, advantageously with the use of strong inorganic bases, e.g., aqueous alkali metal hydroxides or carbonates; or lower alkanols respectively.

The starting material IV is conveniently obtained by condensing compounds of the formulae

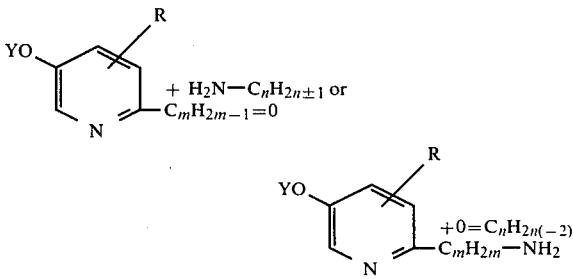

and the aldehydic or ketonic pyridine precursors thereof are similarly obtained as the compounds III, i.e., by condensing said 5-hydroxypicoline metal salts with corresponding alkanoic acid amides or nitriles, e.g., formamide, dimethylacetamide or propionitrile, and hydrolyzing the condensate with water or diluted acids, or hydrogenating it to said amines V. The latter may also be obtained from said aldehydes or ketones by converting them conventionally into their oximes, and reducing them with catalytically activated hydrogen, preferably with the use of rhodium on alumina. If desired, the resulting 5-pyridinols may be esterified, for example with the use of lower alkanoyl, alkanesulfonyl, benzoyl, benzenesulfonyl or benzyloxyformyl halides.

The primary amines V are preferably condensed with said esters derived from strong inorganic acids, such as hydrohalic, e.g., hydrochloric, hydrobromic or advantageously hydriodic acid, or the organic sulfonic acids mentioned above. Said strong bases utilized are preferably tertiary amines, such as tri-lower alkylamines, e.g., di-isopropyl-ethylamine, or cyclic nitrogen bases, such as pyridine or butidine. Care should be taken to avoid a simultaneous quaternization of the resulting secondary amines I, e.g., by avoiding excessive amounts of said reactive esters and/or temperatures excessively above room temperature. The preparation of said compounds V has been described above.

The reduction of the amides VI is conventionally carried out with the stronger light metal hydrides mentioned for said Schiff's bases IV, advantageously alane in solution of said strong bases, or alkali metal aluminum hydrides, e.g., lithium aluminumhydride, lithium or sodium tri-lower alkoxy or bis-alkoxyalkoxy aluminumhydrides, e.g., lithium tri-t-butoxy-aluminumhydride or sodium bis-(2-methoxyethoxy)-aluminumhydride.

The starting material VI is conventionally obtained from said primary amines V and corresponding halides or anhydrides of the acids $C_{n-1}H_{(2n-2)\pm 1}COOH$; or from 5-hydroxypyridyl-2-alkanoic acid halides or anhydrides and the amines $H_2N-C_nH_{2n\pm 1}$.

The compounds of the invention so obtained can be converted into each other according to known methods. For example, resulting unsaturated compounds I with $C_nH_{2n-1}$ being lower alkenyl, may be catalytically hydrogenated, e.g., as mentioned for compounds IV. Any resulting free compound can be converted into a corresponding acid addition salt, for example, by reacting it with an inorganic or organic acid, preferably a pharmaceutically acceptable carboxylic or sulfonic acid, or with a corresponding anion exchange preparation, and isolating the desired salt. An acid addition salt may be converted into the free compound by treatment with a base, e.g., a metal hydroxide, ammonia or a hydroxy ion exchange preparation. Pharmaceutically acceptable acids are, for example, inorganic acids, such as hydrohalic, e.g., hydrochloric, hydrobromic, sulfuric, phosphoric, nitric or perchloric acid, or organic acids, e.g., aliphatic or aromatic carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, pamoic, nicotinic, methanesulfonic, ethanesulfonic, hydroxyethanesulfonic, ethylenesulfonic, benzenesulfonic, halobenzenesulfonic, toluenesulfonic, naphthalenesulfonic, sulfanilic or cyclohexylsulfamic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g., by fractional distillation, crystallization and/or chromatography. Racemic products can likewise be resolved into the optical antipodes, for example, by separation of diastereomeric salts thereof, e.g., by the fractional crystallization of d- or l-camphor sulfonates or mandelates, advantageously those of said Y-esters.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above processes, wherein a compound resulting as an intermediate at any stage thereof, is used as starting material and the remaining steps are carried out, or the process is discontinued at any stage thereof, or in which the starting material is formed under the reaction conditions or is used in the form of its salt or reactive derivatives. For example, in the above-described hydrogenation of compounds IV, or optical resolution, said Y-esters will increase the basicity of the secondary amine, but may hydrolyze under basic reaction, e.g., reduction conditions. Analogously, catalytic hydrogenations of carbobenzoxy compounds III, or Schiff's bases IV with an olefinic $C_nH_{2n-1}$ radical will yield the corresponding saturated $C_nH_{2n+1}$ compounds I. In the process of the invention, those starting materials are advantageously selected which yield the above described preferred embodiments thereof, especially those corresponding to Formula II.

The pharmacologically active compounds of the invention are useful in the manufacture of pharmaceutical compositions comprising an effective amount thereof in conjunction or admixture with excipients suitable for either enteral or parenteral administration Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (b) disintegrants, e.g., starches, agar, alginic acid or its salts, enzymes of the binders or effervescent mixtures and/or (e) adsorbents, colorants, flavors and sweeteners. Injectable compositions are preferably aqueous isotonic solutions or suspensions, and suppositories are advantageously solid fatty emulsions or suspensions. They may be sterilized and/or contan adjuvants, such as preserving, stabilizing, wetting or emulsifying agents, solution promoters, salts for regulating the osmotic pressure and/or buffers. They may also contain other therapeutically valuable substances. Said pharmaceutical compositions are prepared according to conventional mixing, granulating and/or coating methods respectively, and contain about 1 to 75%, preferably 10 to 50%, of the active ingredient.

The following examples, illustrating the invention, are not to be construed as being limitations thereon. Temperatures are given in degrees Centigrade, all parts wherever given are parts by weight and, if not otherwise stated, all evaporations are carried out under reduced pressure, e.g., between 0.1 and 15 mmHg. Azeotropic evaporations are performed with so much of the solvents disclosed, until a clear (anhydrous) distillate is obtained.

EXAMPLE 1

To the mixture of 115 g of 2-methyl-5-pyridinol and 1,500 ml of tetrahydrofuran, 1,350 ml of 1.6 molar n-butyllithium in hexane (2.1 mol) are added while stirring under nitrogen and keeping the temperature between $-15°$ and $0°$. Stirring is continued for 1 hour at $-10°$, whereupon 114 g of isopropyliminoethane are added at such a rate that the temperature remains below $10°$. After stirring the resulting mixture for 1 hour at room temperature, it is divided into 2 portions and one thereof poured into 750 ml of ice water. After thoroughly shaking, the organic layer is separated and the aqueous layer shaken with the other of said 2 portions. The combined organic layers are extracted once with 400 ml of water and discarded. All aqueous solutions are combined, washed three times with 300 ml of diethyl ether and acidified with hydrochloric acid to pH=6-6.5 and washed four times with 300 ml each of ethyl acetate. The aqueous layer is basified with aqueous sodium hydroxide to pH=8.4, saturated with sodium chloride and extracted five times with a total of 2,300 ml of ethyl acetate-isopropanol (1:1). The extract is concentrated, the concentrate twice diluted with isopropanol and concentrated again in order to remove all water azeotropically. The 400 ml of final concentrate are filtered and the filtrate acidified with hydrogen chloride in ethyl acetate to pH=1.5. The precipitate formed is filtered off, washed with isopropanol and recrystallized from 95% aqueous ethanol, to yield to 2-(2-isopropylaminopropyl)-5-pyridinol dihydrochloride melting at 210°-213°.

The starting material is freshly prepared as follows: To 112.5 ml of redistilled acetaldehyde, cooled to $-20°$ to $-30°$, 170.3 ml of isopropylamine are added dropwise while stirring at said temperature. The mixture is stirred for 90 minutes at 0°, whereupon 50 g of potassium hydroxide pellets are added. The mixture is allowed to stand in the cold and decanted off the liquified base. Another 50 g of potassium hydroxide pellets re added twice more and the mixture finally allowed to stand overnight in the refrigerator. The supernatant product is separated, distilled and the fraction boiling at 59°-62° at atmospheric pressure collected, to yield the isopropyliminoethane.

EXAMPLE 2

To the mixture of 26.7 g of 2-(2-isopropylaminopropyl)-5-pyridinol dihydrochloride, 200 ml of methylene chloride and 100 ml of saturated aqueous sodium carbonate, 16 ml of methanesulfonyl chloride are added dropwise while stirring at 0°-10° and adding more sodium carbonate to maintain basicity. Stirring is continued for 30 minutes at pH=9.5-10 and the mixture is combined with half of its volume of saturated aqueous sodium chloride. It is separated, the aqueous layer extracted with methylene chloride, the combined organic solutions washed with saturated aqueous sodium carbonate, dried and evaporated, to yield the 2-(2-isopropylaminopropyl)-5-methanesulfonyloxypyridine as an oil.

39.6 g thereof are dissolved in 200 ml of isopropanol, the solution combined with that of 11.08 g of l-mandelic acid in 68 ml of anhydrous ethanol and the mixture is allowed to stand at room temperature for 20 hours. It is filtered, the filtrate concentrated to 75 ml and again filtered. The combined residues are recrystallized from anhydrous ethanol-methanol (20:3) and then from methanol, to yield the corresponding l-mandelate, melting at 133.5°-134°.

The combined mother liquors are evaporated and 16 g of the residue similarly converted into the d-mandelate, melting at 131.5°-132°.

11.9 g of the l-mandelate are taken up in the minimum amount of water, the solution made basic with saturated aqueous sodium carbonate and extracted with methylene chloride. The extract is dried and evaporated, to yield the corresponding free base. It is taken up in 75 ml of dioxane, 62 ml of 1 N aqueous sodium hydroxide are added and the mixture refluxed for 2 hours while stirring. It is concentrated, the concentrate adjusted with hydrochloric acid to pH=8.4 and saturated with sodium chloride. It is extracted with isopropanolethyl acetate (1:1), the extract evaporated azeotropically, the residue taken up in isopropanol, the solution filtered, acidified with hydrogen chloride in ethyl acetate and the filtrate allowed to stand for 2 days. The precipitate formed is collected and washed with isopropanol, to yield the levorotatory 2-(2-isopropylaminopropyl)-5-pyridinol dihydrochloride, melting at 207°-209°; $[\alpha]_D^{25} = -11.1°$ (water).

Analogously the dextrorotatory antipode is obtained from said d-mandelate, m.p. 209°-210°; $[\alpha]_D^{25} = +10.0°$ (water); it is pharmacologically less active than both the racemic starting material and said levorotatory salt.

EXAMPLE 3

To the solution prepared from 6 g of 5-acetoxy-2-pyridylacetone, 100 ml of methanol and 10 ml of isopropylamine, cooled to room temperature for 10 minutes, 4 g of sodium borohydride are added portionwise during 20 minutes while stirring at room temperature. The mixture is evaporated, the residue taken up in water and the solution washed with chloroform. The aqueous layer is separated, its pH adjusted to 8.4 with hydrochloric acid, and saturated with sodium chloride. It is extracted with ethyl acetate-isopropanol (1:1), the extract evaporated azeotropically with additions of isopropanol and the residue taken up in isopropanol. The suspension is filtered, the filtrate concentrated and its pH adjusted to 1.5 with hydrogen chloride in ethyl acetate. The mixture is refrigerated overnight, the precipitate collected and washed with isopropanol-ethyl acetate, to yield the 2-(2-isopropylaminopropyl)-5-pyridinol dihydrochloride melting at 207°-209°; it is identical with that obtained according to Example 1.

The starting material is prepared as follows: To the suspension of 32.7 g of 2-methyl-5-pyridinol in 400 ml of tetrahydrofuran, 400 ml of 1.6 molar n-butyllithium in hexane are added during 1 hour while stirring under nitrogen and cooling with ice to maintain the temperature below 10°. Thereupon 29 g of dimethylacetamide in 50 ml of tetrahydrofuran are added during 15 minutes, the mixture is stirred for 2 hours at room temperature and poured into 700 ml of water. It is thoroughly shaken, the aqueous layer separated, washed with diethyl ether, acidified with hydrochloric acid and again washed with diethyl ether. Its pH is adjusted to 5.0 with aqueous sodium bicarbonate and after saturation with sodium chloride the mixture is extracted with ethyl acetate-isopropanol (1:1). The extract is evaporated azeotropically with the aid of benzene and the residue is taken up in 100 ml of acetic anhydride. The mixture is stirred for 30 minutes at the steam bath, evaporated, the residue distilled and the fraction boiling at 130°–138°/0.9 mmHg collected, to yield the 5-acetoxy-2-pyridylacetone; its hydrochloride melts at 69°–72° and the oxime thereof at 149°–150°.

EXAMPLE 4

To the suspension of 10.9 g of 2-methyl-5-pyridinol in 200 ml of tetrahydrofuran, 150 ml of 1.6 molar n-butyllithium in hexane are added during 30 minutes while stirring under nitrogen at −20°. After one hour 25 g of 1-isopropyliminopropane are added during 30 minutes at said temperature, the mixture is stirred for 90 minutes and allowed to warm to room temperature. It is poured into 150 ml of water, the organic layer washed with 50 ml of water and the combined aqueous solutions washed with diethyl ether. The pH thereof is first adjusted to 6.8 with hydrochloric acid, the solution washed once more with ethyl acetate, its pH raised to 7.5 with aqueous sodium carbonate, saturated with sodium chloride and extracted with ethyl acetate-isopropanol (1:1).

The extract is evaporated azeotropically, the residue taken up in ethyl acetate, the solution filtered and acidified to pH=4.5 with isopropanolic hydrogen chloride, to yield the 2-(2-isopropylaminobutyl)-5-pyridinol hydrochloride melting at 141°–143°.

The starting material is prepared as follows: To 58 g of propionaldehyde 59 g of isopropylamine are added while stirring and cooling with ice, followed by 1 ml of concentrated hydrochloric acid. After stirring for 2 hours at room temperature, 50 g of potassium hydroxide pellets are added, the mixture stirred for 5 hours, decanted from the aqueous phase, redried with potassium hydroxide, distilled and the fraction boiling at 84°–86° collected, to yield the 1-isopropyliminopropane.

EXAMPLE 5

To the suspension of 9.8 g of 2-methyl-5-pyridinol in 200 ml of tetrahydrofuran, 135 ml of 1.6 molar n-butyllithium are added during 30 minutes while stirring under nitrogen at −20°. After 3 hours 10 g of t-butyliminoethane are added during 30 minutes at said temperature and the resulting mixture is processed as described in Example 4, except that the final solution is acidified with hydrogen chloride in ethyl acetate, to yield the 2-(2-t-butylaminopropyl)-5-pyridinol dihydrochloride melting at 218°–220°.

EXAMPLE 6

Analogous to the methods described in the previous examples, the following compounds are obtained from equivalent amounts of the corresponding starting materials:

(a) 2-(3-isopropylaminobutyl)-5-pyridinol dihydrochloride, m.p. 274°–276°;

(b) 2-(2-cyclohexylaminopropyl)-5-pyridinol dihydrochloride, m.p. 232°–234°.

EXAMPLE 7

To the suspension of 116 g of 2-(2-isopropylaminopropyl)-5-pyridinol and 310 ml of water, 65 g of fumaric acid are added while stirring at 70° under nitrogen. The resulting clear solution is stirred at 20° overnight, the precipitate formed filtered off and washed 3 times with 15 ml of cold water each. 873 g thereof (from several batches) are dissolved in 2,100 ml of water at 70°, the solution filtered hot and the filtrate stirred at room temperature under nitrogen for 2 days. The resulting suspension is filtered and the residue washed twice with 250 ml of cold water each, to yield the 2-(2-isopropylaminopropyl)-5-pyridinol monofumarate melting at 180°–183° with decomposition.

EXAMPLE 8

To the mixture of 342 g of 2-methyl-5-pyridinol and 4,500 ml of tetrahydrofuran, 384.6 g of 1.6 molar n-butyllithium in hexane are added during 3 hours while stirring under nitrogen and keeping the temperature between −18° and −10°. Stirring is continued for 1 hour at −10°, whereupon 340 g of isopropyliminoethane are added during 5 minutes and the temperature is allowed to raise to 10°. After stirring the resulting mixture overnight at room temperature, it is poured into 4,500 ml of cold water. The organic layer is separated and washed with 1,200 ml of water. The combined aqueous solutions are washed three times with 900 ml of diethyl ether each and acidified with 900 ml of concentrated hydrochloric acid to the pH=6.0, which is re-adjusted to 8.0 with 853 g of sodium bicarbonate. The mixture is evaporated at 60°, the residue suspended in 2,400 ml of isopropanol at 60°, the suspension filtered and the filtrate evaporated at 60°. The residue is taken up in 800 ml of water, the mixture cooled to 10°, filtered and the filtrate again evaporated at 60°.

232 g of the precipitate are dissolved in 450 ml of ethanol at 65°, the solution filtered hot, the filtrate cooled to 27° and combined with 380 ml of 6 N ethanolic hydrogen chloride while stirring and cooling to 10°. After 18 hours the suspension is filtered and the residue washed with 50 ml of cold ethanol, to yield the 2-(2-isopropylaminopropyl)-5-pyridinol dihydrochloride melting at 214–216; it is identical with that of Example 1.

The starting material is prepared as follows: To 268.8 g of acetaldehyde, cooled to −25°, 357.6 g of isopropylamine are added during 2 hours while stirring at said temperature under nitrogen. The mixture is stirred for 2 hours at 0°, whereupon 150 g of potassium hydroxide pellets are added. The mixture is allowed to stand for 2 hours, the supernatant is decanted off and treated with another 150 g of potassium hydroxide. After standing at 0° for 2 hours it is decanted onto 150 g of potassium hydroxide and the mixture is allowed to stand overnight at 10°. The supernatant product is separated, distilled at atmospheric pressure and the fraction boiling at 59°–64° collected, to yield the isopropyliminoethane.

EXAMPLE 9

To the solution of 159 g of 2-(2-isopropylaminopropyl)-5-pyridinol dihydrochloride in 1,000 ml of water, 163 g of sodium bicarbonate are added and the suspension evaporated. The residue is suspended in 453 ml of anhydrous ethanol at 60°, the suspension is filtered, the residue washed 3 times with 150 ml of anhydrous ethanol each and the combined filtrates are evaporated, to yield the 2-(2-isopropylaminopropyl)-5-pyridinol melting at 135°–138°.

EXAMPLE 10

To the solution of 1.55 g of 5-hydroxy-2-pyridylacetone in 50 ml of methanol are consecutively added 0.61 g of 2-propenylamine, 2.0 ml of 5.5 N ethereal hydrogen chloride and 0.5 g of sodium cyanoborohydride in this order, while stirring at room temperature. The mixture is stirred for seven days at room temperature, whereupon its pH is adjusted to 1 by the careful addition of 2 N hydrochloric acid. The acidic mixture is evaporated, the residue dissolved in 20 ml of water and the pH of the solution adjusted to 8 with solid sodium bicarbonate. It is evaporated, the residue triturated with isopropanol and dissolved in 25 ml of acetone. The solution is filtered, combined with 1.28 g of fumaric acid in the minimum amount of hot acetone, and the resulting solid filtered off, to yield the 2-[2-(2-propenylamino)-propyl]-5-pyridinol fumarate melting at 194°–195°.

The starting material is prepared as follows: The mixture of 103.6 g of 5-acetoxypyridyl-2-acetone, 0.75 g of anhydrous potassium carbonate and 400 ml of anhydrous ethanol is refluxed for 24 hours, filtered, concentrated to 100 ml, the concentrate cooled and the precipitate collected, to yield the 5-hydroxy-2-pyridylacetone melting at 119°–120°.

EXAMPLE 11

To the solution of 0.8 g of 5-hydroxy-2-pyridylacetone in 25 ml of methanol, 0.33 g of cyclopropylamine, 1 ml of 5 N ethereal hydrogen chloride and 1.16 g of sodium cyanoborohydride are added in this order and the mixture is stirred at room temperature for 3 days. The pH thereof is then adjusted to 1 with 5 N ethereal hydrogen chloride, and then to 8 with solid sodium bicarbonate. The mixture is filtered, evaporated and the residue chromatographed on silica gel with ethyl acetate-methanol (4:1) as eluant, to yield 2-(2-cyclopropylaminopropyl)-5-pyridinol. It is converted into its monofumarate as shown in Example 7, melting at 161° with decomposition.

EXAMPLE 12

To the solution of 1.62 g of 2-(2-aminopropyl)-5-pyridinol hydrochloride in 50 ml of methanol, 0.83 g of n-hexanal are added, followed by 1.75 g of sodium cyanoborohydride, and the mixture is stirred at room temperature for 3 days. The pH thereof is first adjusted to 1 by the addition of 5 N ethereal hydrogen chloride, and then to 8 by the addition of solid sodium bicarbonate. The mixture is filtered, evaported and the residue triturated with isopropanol, to yield the oily 2-(2-n-hexylaminopropyl)-5-pyridinol, showing peaks in the mass-spectrum at 151, 128 and 109 m/e.

The starting material is prepared as follows: The mixture of 8.64 g of 5-hydroxy-2-pyridylacetone, 4.08 g of hydroxylamine hydrochloride and 170 ml of anhydrous ethanol is refluxed for 64 hours and evaporated. The residue is taken up in the minimum amount of ethanol, the solution filtered and the filtrate evaporated, to yield the 2-(2-oximinopropyl)-5-pyridinol hydrochloride melting at 141°–145°.

The mixture of 12.0 g thereof, 500 ml of saturated ammoniacal methanol and 2.4 g of rhodium on alumina is hydrogenated at room temperature and atmospheric pressure for 3 weeks. It is filtered and the filtrate evaporated, to yield the 2-(2-aminopropyl)-5-pyridinol hydrochloride, which is used as such.

A small amount thereof in methanol is acidified with fumaric acid and the precipitate recrystallized from ethyl acetate-ethanol, to yield the corresponding fumarate melting at 171°–176°.

EXAMPLE 13

To the solution of 0.27 g of 2-(2-aminopropyl)-5-pyridinol dihydrochloride and 0.5 ml of di-isopropylethylamine in 0.5 ml of methanol, 0.24 g of isopropyl iodide are added at room temperature while stirring. After 24 hours the mixture is evaporated and the residual salts converted into the 2-(2-isopropylaminopropyl)-5-pyridinol, melting at 135°–138°, as described in Example 9, both free bases, so obtained, are identical.

The starting material is prepared as follows: The solution of 0.19 g of 2-(2-aminopropyl)-5-pyridinol hydrochloride in 10 ml of anhydrous ethanol is combined with 0.2 ml of 5 N ethereal hydrogen chloride and evaporated, to yield the 2-(2-aminopropyl)-5-pyridinol dihydrochloride melting at 125°–128° with decomposition.

EXAMPLE 14

To the solution of 0.39 g of 5-acetoxy-2-(2-acetylaminopropyl)-pyridine in 20 ml of anhydrous tetrahydrofuran, 3.6 ml of a 1 molar solution of alane-triethylamine in toluene are added dropwise while stirring at 0°. After 12 hours 22 ml of 2 N aqueous sodium hydroxide are added at 0°, and the mixture evaporated azeotropically with isopropanol. The residue is taken up in 50 ml of methanol, the pH of the solution adjusted to 8 with 5 N ethereal hydrogen chloride, the resulting salts filtered off, and the filtrate evaporated. The residue is triturated with isopropanol, to yield the 2-(2-ethylaminopropyl)-5-pyridinol melting at 75°–79°.

The starting material is prepared as follows: To the suspension of 1.01 g of 2-(2-aminopropyl)-5-pyridinol hydrochloride in 40 ml of methylene chloride, 3.3 ml of pyridine are added, followed by 1.47 g of acetyl chloride while stirring at room temperature. After 17 hours an equal volume of saturated aqueous sodium bicarbonate is added, the organic layer separated, dried and evaporated. The residual oil is chromatographed on silica, using methanolethyl acetate (4:1) as eluant, to yield the 5-acetoxy-2-(2-acetylaminopropyl)-pyridine, showing in the IR-spectrum peaks at 1758 and 1658 cm$^{-1}$.

EXAMPLE 15

The solution of 0.15 g of dibenzoyl-2-(2-methylaminopropyl)-5-pyridinol in 5 ml of 5 N hydrochloric acid is refluxed for 23 hours, cooled, twice washed with 5 ml of diethyl ether and evaporated, to yield the 2-(2-methylaminopropyl)-5-pyridinol dihydrochloride, showing in the mass-spectrum peaks at 165, 151, 109 and 58 m/e.

The starting material is prepared as follows: The mixture of 0.5 g of 2-(2-aminopropyl)-5-pyridinol hydrochloride, 0.85 g of benzoyl chloride, 10 ml of methylene chloride and 10 ml of saturated aqueous sodium bicarbonate is stirred at room temperature for 1 hour. The organic phase is separated, dried evaporated and the residue recrystallized from diethyl ether to give the dibenzoyl-2-(2-aminopropyl)-5-pyridinol melting at 110°–112°.

0.36 g thereof are dissolved in 1.5 ml of dimethylformamide and the solution added to a slurry of 36 mg of sodium hydride in 1 ml of dimethylformamide at room temperature. The mixture is heated for 15 minutes, allowed to cool to room temperature during one hour and cooled to 0°. It is diluted with 1 ml of toluene and 0.36 g of methyl iodide are added rapidly. The mixture is stirred at room temperature for 1 hour, whereupon 20 ml of water are added. It is extracted twice with 20 ml of diethyl ether and the extract evaporated, to yield the oily, dibenzoyl-2-(2-methylaminopropyl)-5-pyridinol, showing in the NMR a peak at 3.48 ppm.

0.15 g thereof may be partially alcoholyzed in 4 ml of anhydrous methanol in the presence of 15 mg of potassium carbonate while stirring at room temperature for 12 hours, to yield the 2-(N-benzoyl-2-methylaminopropyl)-5-pyridinol, which may replace said dibenzoyl compound in the initial acid hydrolysis.

Similarly, the mixture of 0.1 g of dibenzoyl-2-(2-isopropylaminopropyl)-5-pyridinol and 10 ml of 5 N hydrochloric acid may be refluxed for three days, cooled, filtered, evaporated and the residue triturated with acetone, to yield the 2-(2-isopropylaminopropyl)-5-pyridinol dihydrochloride melting at 199°–204°; it is identical with that obtained according to Examples 1, 3 and 8.

EXAMPLE 16

The mixture of 0.08 g of 2-(N-carbobenzyloxy-2-methylaminopropyl)-5-pyridinol and 2.5 ml of 5 N hydrochloric acid is refluxed for 23 hours, cooled and extracted with diethyl ether. The extract is dryed and evaporated, to yield the 2-(2-methylaminopropyl)-5-pyridinol dihydrochloride, which is identical with that obtained according to Example 15.

The starting material is prepared as follows: To the solution of 0.5 g of 2-(2-aminopropyl)-5-pyridinol, 10 ml of methylene chloride and 10 ml of saturated aqueous sodium bicarbonate, 1.04 g of benzyl chloroformate are added while stirring at room temperature. After 12 hours the organic phase is separated, dried, evaporated and the residue crystallized from diethyl ether-hexane, to yield the bis-carbobenzyloxy-2-(2-aminopropyl)-5-pyridinol melting at 63°–65°.

The solution of 0.42 g thereof in 2 ml of dimethylformamide is added to the slurry of 36 mg of sodium hydride in 1.5 ml of dimethylformamide and the mixture is warmed to 55° for 1 hour. It is allowed to cool to 25° for 4 hours, cooled to 0°, diluted with 1 ml of toluene and 0.36 g of methyl iodide are added. The mixture is stirred at room temperature for 12 hours, whereupon 10 ml of disodium phosphate buffer are added. The aqueous phase is extracted twice with 20 ml of diethyl ether, the extract washed with water, dried and evaporated, to yield the bis-carbobenzyloxy-2-(2-methylaminopropyl)-5-pyridinol and the 2-(N-carbobenzyloxy-2-methylaminopropyl)-5-pyridinol in approximately equal quantities. Said mixture is taken up in ethyl acetate, the solution extracted with N aqueous sodium hydroxide and the aqueous layer separated. Its pH is adjusted to 8 with monosodium phosphate buffer, the mixture extracted with diethyl ether, the extract dried and evaporated, to yield the 2-(N-carbobenzyloxy-2-methylaminopropyl)-5-pyridinol.

EXAMPLE 17

The mixture of 0.08 g of 2-(N-carbobenzyloxy-2-methylaminopropyl)-5-pyridinol, 5 ml of anhydrous ethanol saturated with anhydrous hydrogen chloride and 0.04 g of 10% palladium on charcoal is hydrogenated at room temperature and atmospheric pressure for 18 hours. It is filtered, the residue washed with ethanolic hydrogen chloride and the filtrate evaporated, to yield the 2-(2-methylaminopropyl)-5-pyridinol dihydrochloride, which is identical with that of Examples 15 and 16.

EXAMPLE 18

Preparation of 10,000 tablets, each containing 100 mg of the active ingredient:

| Formula: | |
|---|---|
| 2-(2-isopropylaminopropyl)-5-pyridinol dihydrochloride | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure

All powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets using concave punches with 10.3 mm diameter, uppers bisected.

EXAMPLE 19

Preparation of 1,000 capsules each containing 50 mg of the active ingredient:

| Formula: | |
|---|---|
| 2-(2-isopropylaminopropyl)-5-pyridinol monofumarate | 50.00 g |
| Modified corn starch | 5.00 g |
| Lactose | 143.75 g |
| Magnesium stearate | 1.00 g |
| Surfactant | 0.25 g |

Procedure

All the powders are passed through a screen with openings of 0.6 mm. Then the drug substance is mixed first with the magnesium stearate and surfactant, whereupon the starch and lactose are added and mixed until homogeneous. No. 2 capsules are filled with 200 mg each, using a filling machine.

Analogously tablets or capsules are prepared, containing another compound of the invention e.g., as illustrated by the previous examples herein.

What is claimed is:

1. Secondary 2-aminoalkyl-5-pyridinols of the formula

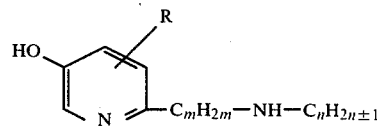

wherein R is hydrogen or methyl, m is an integer from 2 to 4 and n is an integer from 1 to 7; or a pharmaceutically acceptable acid addition salt thereof.

2. A compound as claimed in claim 1, in which formula R is hydrogen or methyl, m is the integer 2 or 3, and n is an integer from 2 to 6; or a pharmaceutically acceptable acid addition salt thereof.

3. A compound as claimed in claim 1 and corresponding to the formula

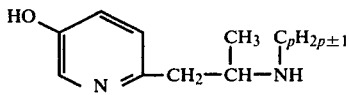

wherein p is an integer from 3 to 6; or a pharmaceutically acceptable acid addition salt thereof.

4. A compound as claimed in claim 3, in which formula $C_pH_{2p\pm1}$ represents i-propyl, t-butyl, allyl or cyclopropyl; or a pharmaceutically acceptable acid addition salt thereof.

5. A compound as claimed in claim 4 and being the 2-(2-isopropylaminopropyl)-5-pyridinol, or a pharmaceutically acceptable acid addition salt thereof.

6. A compound as claimed in claim 1, and being the levorotatory optical antipode thereof.

7. A cardioprotective pharmaceutical composition comprising a correspondingly effective amount of a compound claimed in claim 1, together with a pharmaceutical excipient.

8. A method of alleviating cardiac ischemia in mammals, which consists in administering to them enterally or parenterally a cardioprotective amount of a composition as claimed in claim 7.

* * * * *